(12) United States Patent
Itou

(10) Patent No.: US 8,172,774 B2
(45) Date of Patent: May 8, 2012

(54) GUIDE WIRE

(75) Inventor: Yutaka Itou, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1084 days.

(21) Appl. No.: 12/051,950

(22) Filed: Mar. 20, 2008

(65) Prior Publication Data

US 2008/0234606 A1    Sep. 25, 2008

Related U.S. Application Data

(60) Provisional application No. 60/908,066, filed on Mar. 26, 2007.

(30) Foreign Application Priority Data

Mar. 23, 2007    (JP) ................. 2007-077918

(51) Int. Cl.
*A61M 25/00*    (2006.01)
(52) U.S. Cl. ........................................ 600/585
(58) Field of Classification Search ............... 600/433, 600/434, 585; 604/164.13
See application file for complete search history.

(56) References Cited

U.S. PATENT DOCUMENTS

| | | |
|---|---|---|
| 3,906,938 A | 9/1975 | Fleischhacker |
| 4,925,445 A | 5/1990 | Sakamoto et al. |
| 5,069,226 A | 12/1991 | Yamauchi et al. |
| 5,238,004 A | 8/1993 | Sahatjian |
| 5,269,759 A | 12/1993 | Hernandez et al. |
| 5,299,580 A | 4/1994 | Atkinson et al. |
| 5,368,049 A * | 11/1994 | Raman et al. ........ 600/585 |
| 5,402,799 A | 4/1995 | Colon et al. |
| 5,411,476 A | 5/1995 | Abrams et al. |
| 5,452,726 A | 9/1995 | Burmeister |
| 5,497,786 A | 3/1996 | Urick |
| 5,498,250 A | 3/1996 | Prather |
| 5,772,609 A | 6/1998 | Nguyen et al. |
| 5,797,857 A | 8/1998 | Obitsu |
| 5,876,356 A | 3/1999 | Viera et al. |
| 5,924,998 A | 7/1999 | Cornelius et al. |
| 5,951,494 A | 9/1999 | Wang et al. |
| 6,001,068 A | 12/1999 | Uchino et al. |
| RE36,628 E | 3/2000 | Sagae et al. |
| 6,093,157 A | 7/2000 | Chandrasekaran |
| 6,165,292 A | 12/2000 | Abrams et al. |
| 6,234,981 B1 | 5/2001 | Howland |
| 6,390,992 B1 | 5/2002 | Morris et al. |
| 6,520,923 B1 | 2/2003 | Jalisi |
| 6,679,853 B1 | 1/2004 | Jalisi |
| 2004/0030266 A1 | 2/2004 | Murayama et al. |
| 2004/0039308 A1 | 2/2004 | Murayama et al. |
| 2004/0039309 A1 | 2/2004 | Murayama et al. |
| 2004/0181174 A2 * | 9/2004 | Davis et al. ........ 600/585 |
| 2005/0152731 A1 | 7/2005 | Mishima et al. |

FOREIGN PATENT DOCUMENTS

JP    7-10761 Y2    3/1995

* cited by examiner

*Primary Examiner* — Max Hindenburg
*Assistant Examiner* — Jonathan M Foreman
(74) *Attorney, Agent, or Firm* — Buchanan Ingersoll & Rooney PC

(57) ABSTRACT

A guide wire includes a wire body having a plate-shaped reshapeable section at a distal part thereof, wherein the reshapeable section is provided along the longitudinal direction thereof with a plurality of bent parts bent in opposite directions. At least one of the bent parts is more susceptible to plastic deformation than other parts of the reshapeable section.

14 Claims, 6 Drawing Sheets

GUIDE WIRE

This application claims priority under 35 U.S.C. §119(e) to U.S. Provisional Application No. 60/908,066 filed on Mar. 26, 2007, the entire content of which is incorporated herein by reference. This application is also based on and claims priority to Japanese Application No. 2007-77918 filed on Mar. 23, 2007, the entire content of which is incorporated herein.

TECHNICAL FIELD

The present invention generally pertains to elongated medical devices. More specifically, the invention pertains to a guide wire.

BACKGROUND DISCUSSION

Guide wires are used to insert and guide a catheter to a target site for use in treatment of cites at which open surgery is difficult or which require low invasiveness to the body or in examination or treatment of a cardiac disease through cardio-angiography or the like.

For example, in the process of PCI (Percutaneous Coronary Intervention), a treatment is conducted as follows. The distal end (tip) of a guide wire protruding from the distal end of a balloon catheter is inserted together with the balloon catheter to a position immediately on the proximal side of a stenosed portion of the coronary artery, which portion is the target site, under fluoroscopic observation. Next, the distal end of the guide wire is passed through the stenosed portion. Thereafter, the balloon of the balloon catheter is guided to the stenosed portion while still positioned along the guide wire, and the balloon is expanded to dilate the stenosed portion, thereby recovering a quantity of bloodstream flow.

For instance, in order to insert a guide wire from a femoral artery and advance it through an aorta, an aortic arch and a coronary artery orifice into the coronary artery by the Seldinger technique, it is desirable that the guide wire be excellent in flexibility for following the blood vessels (trackability) and in pushability which ensures effective transmission of a pushing force from the operator's hand (the proximal side) to the distal part of the guide wire.

In addition, for the purpose of advancing the guide wire into a desired branch at a branching part of the coronary artery or the like, a distal part of the guide wire may in some cases be shaped in conformity with the shape of the branching part. Such a shaping operation is ordinarily performed with the surgeon's fingers at the time of surgery, and is called "reshaping".

Especially in the case of inserting the distal end of a guide wire into the coronary artery on the peripheral side, it may in many cases be impossible to select the desired branch while using the angle- or J-type tip shape of the guide wire preformed according to the known art, and the guide wire tip may be reshaped into a desired shape and then inserted again. When the shape of the guide wire tip is not satisfactory for the intended selection of the desired branch, it is necessary to withdraw the guide wire from the catheter, reshape the guide wire tip again and then insert the guide wire once again.

There is also known a guide wire in which a wire body is composed of a Ni—Ti alloy exhibiting superelasticity, for obtaining flexibility at the distal part of the guide wire. In this case, however, the superelasticity of the distal part of the wire body makes the reshaping difficult. In view of this, there has been developed a guide wire having a reshapeable distal part.

A guide wire in which a distal part of a core wire (wire body) composed of a superelastic alloy has had its superelasticity degraded by heat treatment is disclosed in, for example, U.S. Pat. No. 5,452,726.

However, in the case where the superelasticity of the distal part is degraded by heat treatment, the distal part provided easily with a new shape upon reshaping may return to its original shape by losing the new shape upon being inserted into a living body. This is because the superelastic alloy tends to return to its original straight shape due to its own shape memory effect. More specifically, the heat treatment raises the transformation temperature of the distal part, and the heat-treated part does not exhibit superelasticity at room temperature, so that this part can be shaped as if it were plastically deformed. However, the deformation in this instance is an apparent plastic deformation. Therefore, when the reshaped part is inserted into the living body and is warmed up to the body temperature, its transformation temperature is approached and it returns to the original straight shape.

Proposals have also been made for a guide wire in which the superelasticity of the distal part of a core wire (wire body) is deprived by cold drawing. An example is described in U.S. Pat. No. 5,238,004.

However, in the case where superelasticity is lost by cold drawing, the effect may often be unsatisfactory and so reshaping may be difficult to achieve. In addition, the worked part may become harder than required, thereby lowering the flexibility of the distal part of the guide wire. In order to enhance the flexibility, it may be contemplated to set a flat plate-like section (reshapeable section) to be thinner. In that case, however, the strength of the flat plate-like section cannot be maintained. Since the guide wire tip may be advanced through a stenosed portion while being rotated or may be pulled in a bent state, it must have a strength (e.g., tensile strength) not lower than a certain value. Therefore, there is a limit to the thinning of the flat plate-like section. Accordingly, by this approach it is quite difficult, if not impossible, to secure both flexibility and strength.

SUMMARY

A guide wire comprises or includes a wire body having a plate-shape reshapeable section at a distal part of the reshapeable section. According to one aspect, the reshapeable section is configured to include a plurality of bent parts disposed longitudinally along the reshapeable section and bent in opposite directions. At least one of the bent parts is more susceptible to plastic deformation than other parts of the reshapeable section.

The bent part more susceptible to plastic deformation preferably has undergone work hardening or has been annealed. Also, the bent part more susceptible to plastic deformation can include a malleable metal secured to a recessed part side of the bent part.

The reshapeable section preferably has a part where the plate thickness and/or the plate width decreases continuously or stepwise along the distal direction. The reshapeable section preferably has a part where the interval between the adjacent bent parts decreases along the distal direction. The part including the reshapeable section of the wire body may be composed of a superelastic alloy. The wire body preferably has a tapered section of which the outer diameter gradually decreases along the distal direction. The tapered section may be formed on the distal side of and in the vicinity of the reshapeable section. The guide wire preferably further includes a coil which covers the reshapeable section. The guide wire preferably includes fixing materials for fixing the coil to the wire body at a plurality of locations, wherein one of the plurality of fixing materials is disposed on the distal side of the reshapeable section, and another of the plurality of fixing materials is disposed on the proximal side of the reshapeable section.

The guide wire here possesses a distal part possessing excellent reshapeability characteristics allowing the distal part to be relatively easily and assuredly reshaped into a desired shape while securing sufficient flexibility of its distal part.

The reshapeable section is not fabricated in a way which imparts easier plastic deformation characteristics to the entire reshapeable section. rather, the reshapeable section is configured to be more easily plastically deformable in only spaced apart parts of the reshapeable section, specifically only at the spaced apart bent parts. Therefore, it is possible to avoid situations in which the entirety of the reshapeable section is hardened more than required in a manner lowering the flexibility and elasticity of the distal part of the guide wire.

By appropriately setting the shape (the plate thickness, the plate width, the interval between the adjacent bent parts) of the reshapeable section, the degree of plastic deformability of the bent parts and other related factors, a desired portion (for example, a portion on the distal side) of the reshapeable section can be reshaped into a more complicated shape or fine shape.

BRIEF DESCRIPTION OF THE DRAWING FIGURES

DETAILED DESCRIPTION

Figure 1:
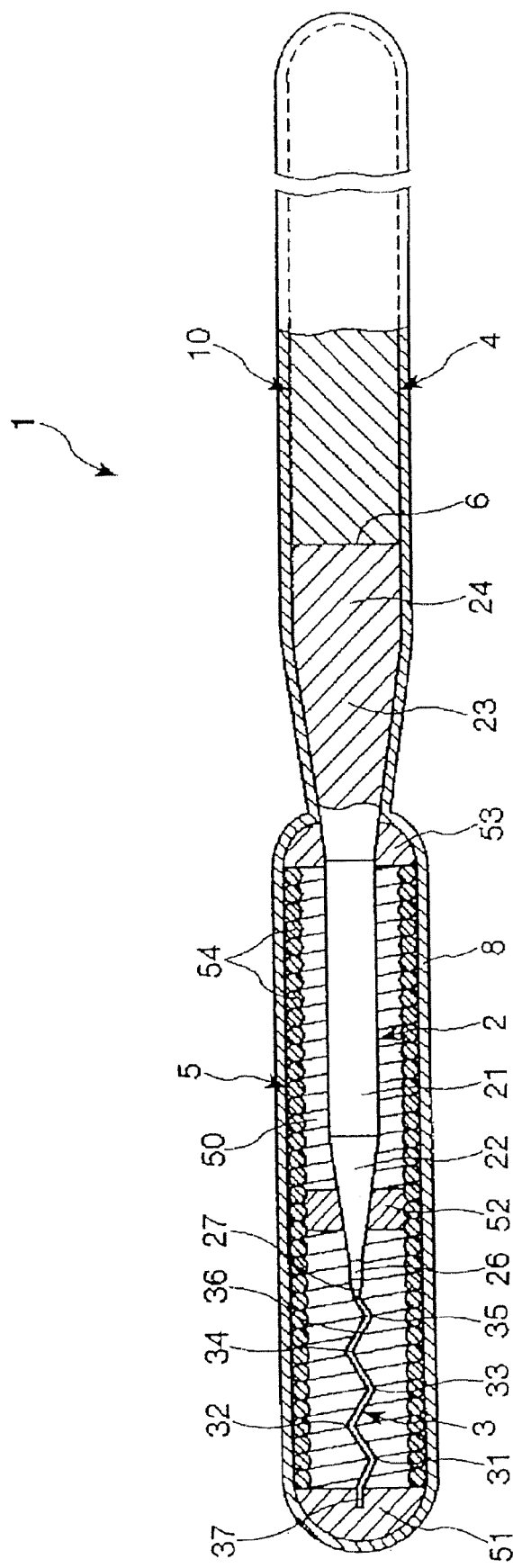
FIG. 1 is a partial longitudinal cross-sectional view of a first embodiment of the guide wire disclosed here.
Figure 2:
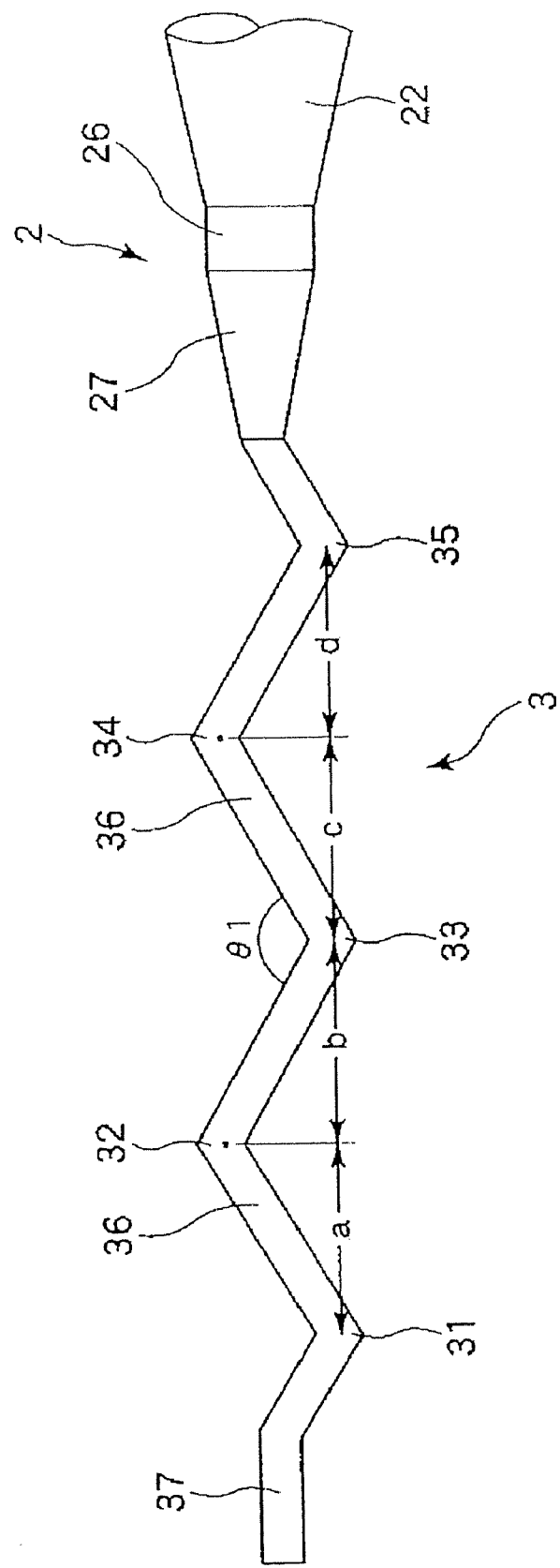
FIG. 2 is a side view of a reshapeable section of the guide wire shown in FIG. 1.
Figure 3:
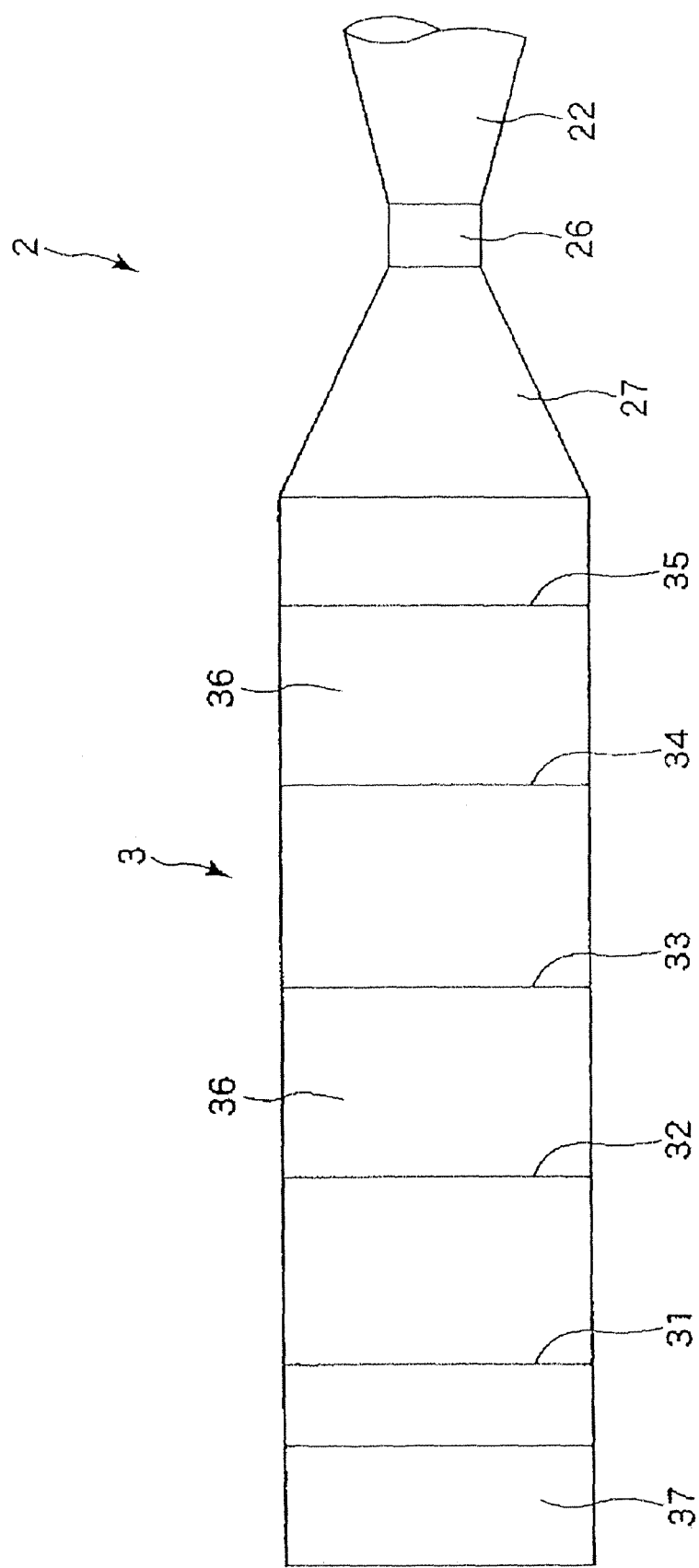
FIG. 3 is a plan view of the reshapeable section of the guide wire shown in FIG. 1.

One embodiment of the guide wire disclosed here is described below and illustrated in FIGS. 1-3. The right side in FIGS. 1-3 is referred to as the "proximal" side or part, while the left side is referred to as the "distal" side or part. In addition, to help facilitate an understanding of the disclosure here, the guide wire shown in FIGS. 1-3 is schematically shown in the state of being shortened in the longitudinal direction and exaggerated in the diameter direction (thickness direction). Thus, it is to be understood that the ratio between the size in the longitudinal direction and the size in the diameter direction in the drawings is different from the actual ratio.

The guide wire 1 shown in FIG. 1 is a catheter guide wire configured to be inserted in the lumen of a catheter (inclusive of endoscopes). According to this illustrated embodiment, the guide wire includes a wire body 10 and a helical coil 5 disposed at the distal part (distal-side part) of the wire body 10. The wire body 10 is comprised of, or includes, first and second wires 2, 4 joined to each other. The first wire 2 is disposed on the distal side or the distal portion of the guide wire, and the second wire 4 is disposed on the proximal side of the first wire 2. The overall or total length of the guide wire 1 is not particularly limited, and is preferably about 200 to 5000 mm.

The first wire 2 is composed of a wire material which is flexible or elastic. In the present embodiment, the first wire 2 includes a constant outer diameter section 21, a first tapered section 22, a distal-side constant outer diameter section 26, a plate-like transition section 27, a reshapeable section, a large diameter section 24, and a second tapered section 23. The constant outer diameter section 21 possesses an outer diameter that is constant (inclusive of substantially constant). The first tapered section 22 is located on the distal side relative to the constant outer diameter section 21 and possesses an outer diameter that gradually decreases along the distal direction. The distal-side constant outer diameter section 26 is located on the distal side relative to the first tapered section 22 and possesses an outer diameter that is constant (inclusive of substantially constant). The plate-like transition section 27 is located on the distal side of the distal-side constant outer diameter section 26 and possesses a decreasing thickness and increasing width along the distal direction. The reshapeable section 3 is located on the distal side of the transition section 27. The large diameter section 24 is located on the proximal side of the constant outer diameter section 21 and possesses an outer diameter larger than the constant outer diameter section 21. As illustrated, the large diameter section 24 can possess an outer diameter that is constant (inclusive of substantially constant). The second tapered section 23 is located between the constant outer diameter section 21 and the large diameter section 24, and possesses a gradually decreasing outer diameter along the distal direction. These sections of the first wire 2 are sequentially disposed, beginning at the distal end of the wire 2, in the following order—the reshapeable section 3, the transition section 27, the distal-side constant outer diameter section 26, the first tapered section 22, the constant outer diameter section 21, the second tapered section 23 and the large diameter section 24.

With the first tapered section 22 positioned between the reshapeable section 3 and the constant outer diameter section 21, particularly with the reshapeable section 3 formed on the distal side of and in the vicinity of the first tapered section 22, the rigidity (flexural rigidity, torsional rigidity) of the first wire 2 is gradually reduced along the distal direction. As a result, the guide wire 1 is provided with a good crossability of the stenosed portion, meaning the guide wire is well suited to crossing the stenosed portion of a blood vessel. In addition, the flexibility at the distal part of the guide wire is enhanced, whereby trackability of the guide wire along blood vessels and the like, and safety, are enhanced. Also, kinking and the like are inhibited, preferably prevented.

In addition, like in the case of the first tapered section 22, with the second tapered section 23 disposed so that the constant outer diameter section 21 and the large diameter section 24 are connected through the second tapered section 23, the rigidity (flexural rigidity, torsional rigidity) of the first wire 2 is gradually decreased along the distal direction.

The taper angle (the rate of decrease in outer diameter) of the first tapered section 22, and also the second tapered section 23, may be constant along the longitudinal direction of the wire body 10 or may vary along the longitudinal direction at part of the first tapered section 22 or the second tapered section 23. For example, a plurality of portions having a comparatively large taper angle (rate of decrease in outer diameter) and a plurality of portions having a comparatively small taper angle may be formed alternately and repeatedly.

Also, the taper shape and/or taper angle of the first tapered section 22 and the second tapered section 23 may be different.

The reshapeable section 3 configured as described below is positioned on the distal side of the first tapered section 22, with both the distal-side constant outer diameter section 26 and the transition section 27 located between the reshapeable section 3 and the first tapered section 22. The reshapeable section 3 is preferably integrally formed in one piece with the first tapered section 22 (i.e., the two sections form an integral one-piece body). Here, the first wire 2 along its entire extent, from the distal end to the proximal end and inclusive of the reshapeable section 3, is integrally formed of the same material. As will be described below in more detail, a preferable material constituting the first wire 2 is a superelastic alloy (an alloy exhibiting pseudo-elasticity) represented by Ni—Ti alloy. Therefore, a preferable material of the reshapeable section 3 is also a superelastic alloy. Such a construction will be described below in more detail. Generally speaking, the guide wire is comprised of coaxially disposed distal and proximal portions, with the reshapeable section 3 forming at least a part of the distal portion of the guide wire.

As shown in FIGS. 2 and 3, the reshapeable section 3 is plate-shaped, possessing a thickness less than the width. The reshapeable section 3 is used (e.g., in a medical procedure) after being deformed into a desired shape (after reshaping). Generally, a guide wire may in some cases be used after its distal part is preliminarily deformed by a surgeon or the like into a desired shape, for purposes of conforming the distal part of a catheter or the like to be guided to the shape of a blood vessel or for purposes of achieving appropriate and smooth selection of, and guided movement into, a desired blood vessel branch. The bending of the distal part of the guide wire into a desired shape in this manner is called "reshaping". The reshapeable section 3 allows he reshaping to be carried out relatively easily and assuredly, whereby operationality (manipulability) in inserting the guide wire 1 into a living body is enhanced remarkably.

The plate-like reshapeable section 3 is provided along its longitudinal extent with a plurality of bent parts which are bent in opposite directions. In this embodiment, and as bets illustrated in FIG. 2, the reshapeable section 3 has a total of five bent parts, namely, bent parts 31, 32, 33, 34 and 35 in this order from the distal side. Of these bent parts, the bent parts 31, 33 and 35 are so bent as to project to the lower side in FIG. 2, whereas the bent parts 32 and 34 are so bent as to project to the upper side in FIG. 2. Thus, the overall shape of the reshapeable section 3 is a so-called zig-zag shape which, in the illustrated embodiment, is defined by the spaced bent parts 31-35 and the other parts 36 interposed between adjacent ones of the bent parts. The other parts 36 interposed between the bent parts 31-35 constitute interposed parts 36 oriented such that adjacent ones of the interposed parts 36 are non-coplanar (i.e., the axes or imaginary continuations of the adjacent interposed parts intersect one another).

The plurality of bent parts 31-35 may be produced by suitably forming (applying a pressing force or compressing) a wire portion distally extending from the transition section 27 to obtain a plate-like shape, followed by forming or bending the plate-like shaped portion into bent parts having predetermined shapes. Alternatively, the forming of the plate-like shape and the forming of the bent parts may be performed simultaneously by compressing the wire portion by such dies that the bent parts having the predetermined shapes can be formed. When the wire portion extending from the distal-side constant outer diameter section 26 composed of a superelastic Ni—Ti alloy is formed into a plate-like shape by compression, work hardening may in some cases be induced so that the formed product might not exhibit superelasticity. In such a case, during the forming into the plurality of bent parts 31-35 or after heating conducted subsequent to forming, a mechanism for providing a property for relatively easy plastic deformation as described later can be imparted to the bent parts 31-35.

At least one of the bent parts 31, 32, 33, 34 and 35 (in this embodiment, all the bent parts) has a property for easier plastic deformation as compared with the other parts of the reshapeable section 3 (for example, straight parts 36 between the adjacent bent parts, and the part 37 on the distal side relative to the bent part 31). That is, one or more of the bent parts 31-35 is more easily plastically deformed than other parts of the reshapeable section 3. This helps ensure that when the reshapeable section 3 is reshaped, the bent parts 31-35 are deformed (plastically deformed) with priority to the other parts (i.e., are deformed prior to deformation of the other parts). This helps permit reshaping into the desired shape to be carried out relatively easily and assuredly, and the desired shape achieved by reshaping is maintained. The reshapeable section 3 thus reshaped keeps the reshaped shape, not only at normal temperature but also when its temperature is raised nearly to a body temperature during use.

Examples of the method (means) for rendering the bent parts 31-35 more easily plastically deformed than the other parts include a method in which the bent parts 31-35 are subjected to work hardening, and a method in which the bent parts 31-35 are subjected to a heat treatment (particularly, annealing). In this case, the reshapeable section 3 is subjected to the work hardening or heat treatment, not as a whole but only partially, i.e., only at the parts of the reshapeable section 3 that are to be bent, namely the parts corresponding to the bent parts 31-35.

The work hardening can, for example, be carried out by use of a press or a pressure forming apparatus (die-and-punch, or the like) under a pressure of, for example, 1 to 1000 MPa.

The heat treatment (annealing treatment) can, for example, be conducted by a method in which the parts to be the bent parts 31-35 of the reshapeable section 3 are locally heated by use of a heating wire or a burner having good directivity, followed by cooling such as natural cooling. In this case, the heating temperature may be about 50 to 700° C., and the cooling rate during the cooling may be about 5 to 700° C./min.

In addition, the work hardening and the heat treatment may both be used (i.e., used together in combination) to render the bent parts 31-35 more easily plastically deformed relative to the other parts of the reshapeable section 3. The means for rendering the bent parts 31-35 more easily plastically deformed may further be a method as follows. First, the wire portion distally extending in the distal direction from the transition section 27 composed of a superelastic Ni—Ti alloy is pressed into a plate-like shape, and thereafter the thus formed portion is formed into the bent parts having predetermined shapes. Naturally, the formation of the plate-like shape and the formation of the bent parts may be carried out simultaneously. As above-mentioned, in the case where the compression of the reshapeable section 3 into the plate-like shape is accompanied by work hardening so that the reshapeable section 3 does not exhibit superelasticity, the flat plate parts (the parts 36, etc.) between the adjacent bent parts is subjected to a heart treatment, for example, by irradiation with a laser beam. As a result of this, the bent parts possess characteristics allowing them to be more easily plastically deformed as compared with the flat plate parts (the parts 36, etc.) between the bent parts.

The property allowing a more easy plastic deformation of the bent parts, through work hardening and/or heat treatment, is imparted not to the entire length of the reshapeable section 3, but only to restricted parts of the reshapeable section 3, specifically only the bent parts 31-35. It is thus possible to avoid problems which might otherwise be encountered, i.e., the problem that the reshapeable section 3 as a whole is hardened more than necessary, thereby lowering the flexibility or elasticity of the distal part of the guide wire 1.

As shown in FIG. 2, reshaping is for example conducted so that, when the angle of the inside (valley side) of the bent part 33 before reshaping is θ1, the angle θ2 of the same part after reshaping is about θ1+α° or θ1−α°. Then, this is applied also to the other four bent parts 31, 32, 34 and 35, whereon with a total of five bent parts 31-35, the distal end of the reshapeable section 3 can be bent at ±5α° at maximum in relation to the proximal end of the reshapeable section 3. For example, where α is 18°, the distal end of the reshapeable section 3 can be so bent as to be substantially perpendicular (α×5 or 18°×5) to the proximal end of the reshapeable section 3 (the reshapeable section 3 can be bent into an L-shape). In addition, where a is 36°, the distal end of the reshapeable section 3 can be so bent as to be reversely directed toward the proximal end of the reshapeable section 3 (the reshapeable section 3 can be bent back upon itself so as to possess a U-shape). The value of α can be adjusted, as desired, by selecting the shape and dimensions of parts near the bent parts 31-35, the conditions of work hardening and/or heat treatment, etc.

The shape of the reshapeable section 3 upon reshaping is not limited to the L-shape and the U shape (J shape). Indeed, the shape of the reshapeable section 3 upon reshaping may be any other shape such as S shape and three-dimensional shapes.

Referring to the embodiment shown in FIG. 2, if the intervals between the adjacent ones of the bent parts 31-35 in the reshapeable section 3 are identified as a, b, c and d, then a, b, c and d have equal (inclusive of substantially equal) length values. That is, the bent parts 31-35 are formed at a regular pitch or regular intervals along the longitudinal extent or direction of the reshapeable section 3. The intervals (a, b, c and d) between the adjacent bent parts may all be different, or some of them may be different from the others.

Examples of the just-mentioned configuration include the case where the interval between the adjacent bent parts decreases in the distal direction in some part of the reshapeable section 3, i.e., the intervals a, b, c and d satisfy the relationship of a≦b≦c≦d (exclusive of the case of a=b=c=d). Such a configuration permits the reshapeable section 3 to be reshaped more finely as the distal end is approached, which naturally is preferable. In other words, the reshapeable section 3 can be reshaped into a more complicated shape or finer shape (for example, into a more steeply curved or bent shape) on the distal end side than on the proximal end side.

In the present embodiment, the plate thickness and plate width of the reshapeable section 3 are substantially constant along the longitudinal direction thereof. Specifically, at least the portion including the bent parts 31-35 of the reshapeable section 3 is substantially constant in plate thickness and plate width. It is to be noted, however, that in the present invention this configuration is not limitative, and the plate thickness and/or the plate width may vary at some part(s) of the reshapeable section 3. For example, a configuration may be adopted in which one or more of the bent parts 31-35 (preferably, all of the bent parts) have increased plate thickness and/or plate width as compared with parts other than the bent parts of the reshapeable section 3 (for example, the straight parts 36 between the adjacent bent parts, or the part 37 on the distal side relative to the bent part 31).

In addition, while the vertex of the bent parts 31-35 of the zig-zag shaped reshapeable section 3 are peaked (sharp) in shape in the illustrated embodiment, this configuration is not required. For example, the vertices of some or all of the bent parts 31-35 forming the zig-zag shaped reshapeable section 3 may possess a rounded shape (may be rounded in shape).

In the first wire 2, each of the distal-side constant outer diameter section 26, the constant outer diameter section 21 and the large diameter section 24 has a constant outer diameter along the longitudinal direction of the wire. The outer diameter of the distal-side constant outer diameter section 26 is equal to the minimum outer diameter of the first tapered section 22, and the outer diameter of the constant outer diameter section 21 is equal to the maximum outer diameter of the first tapered section 22 and is equal to the minimum outer diameter of the second tapered section 23. The outer diameter of the large diameter section 24 is substantially equal to the maximum outer diameter of the second tapered section 23. The references to constant and equal include substantially equal and substantially constant.

The distal end of the second wire 4 is joined to the proximal end of the first wire 2 (the proximal end of the large diameter section 24). The second wire 4 is composed of a flexible or elastic wire material.

The method of joining the first wire 2 and the second wire 4 is not particularly limited. Examples of the joining method include welding such as friction welding, welding using a laser, butt resistance welding, e.g., upset welding, etc., and joining by use of a tubular joint member. Among these joining methods, butt resistance welding is particularly preferred since it can be carried out comparatively easily and provides a relatively high joint strength.

In the present embodiment, the second wire 4 is substantially constant in outer diameter. The outer diameter of the second wire 4 is substantially equal to the outer diameter of the large diameter section 24 of the first wire 2. This helps ensure that when the proximal end of the large diameter section 24 of the first wire 2 and the distal end of the second wire 4 are joined to each other, a step resulting from a difference in outer diameter between the wires 2 and 4 does not exist. Instead, a continuous surface can be obtained at the outer periphery of the joint part (weld part) 6 of the wires 2, 4. Nevertheless, it is to be understood that this structure is not a necessary requirement. For example, the outer diameter(s) of the first wire 2 and/or the second wire 4 may vary across the joint part 6.

The outer diameter of the first wire 2 may be smaller than the outer diameter of the second wire 4. This permits the guide wire 1 to be rich in flexibility on the first wire 2 disposed on the distal side and be comparatively high in rigidity on the second wire 4 disposed on the proximal side. Consequently, both flexibility at the distal part and excellent operationality (pushability, torque transmission performance, etc.) can be realized.

The materials constituting the first wire 2 and the second wire 4 are not particularly limited. Examples of the materials which can be used to fabricate the first and second wires 2, 4 here include various metallic materials such as stainless steels (all species of SUS, e.g., SUS304, SUS303, SUS316, SUS316L, SUS316J1, SUS316J1L, SUS405, SUS430, SUS434, SUS444, SUS429, SUS430F, SUS302), piano wire, cobalt alloys, pseudo-elastic alloys (inclusive of superelastic alloys), etc.

The material constituting the first wire 2 is preferably a pseudo-elastic alloy (inclusive of superelastic alloy), more preferably a superelastic alloy.

Superelastic alloys are rich in flexibility, have a restoring property, and have relatively little tendency to undergo irreversible bending. Therefore, with the first wire 2 comprised of a superelastic alloy, the guide wire 1 possesses sufficient flexibility and restoring property on bending, is enhanced in trackability with respect to complicatedly curved or bent blood vessels and the like, and exhibits more excellent operationality. In addition, even when the first wire 2 is repeatedly subjected to curving or bending deformations, the restoring property possessed by the first wire 2 inhibits or prevents the first wire 2 from tending to undergo irreversible bending. The operationality of the guide wire 1 is thus inhibited from being lowered due to a tendency to undergo irreversible bending acquired by the first wire 2 during the use of the guide wire 1.

Possible elastic (superelastic) metals which can be utilized include those elastic metals whose stress-distortion curve by tension has a variety of shapes, and also those elastic metals whose transformation temperatures such as As (austenite start temperature), Af (austenite finish temperature), Ms (martensite start temperature) and Mf (martensite finish temperature) can or cannot be measured. Further, also included are all of those superelastic metals which are deformed (distorted) by a relatively great amount by stress and return to their original shape in response to removal of the stress are included. Thus, superelastic alloys includes those which exhibit different tensile stress vs. strain curves (i.e., the superelastic alloys which can be used here are not limited to superelastic alloys having a particular tensile stress vs. strain curve), those which have transformation points such as As, Af, Ms, Mf, whether they are clearly measurable or not, and those which are largely deformed (strained) under stresses and return to their original shape upon removal of the stresses.

Examples of the preferable composition of the superelastic alloy include Ni—Ti alloys such as a Ni—Ti alloy containing 49 to 52 at % of Ni, Cu—Zn alloys containing 38.5 to 41.5 wt % of Zn, and Cu—Zn—X alloys containing 1 to 10 wt % of X (X is at least one selected from among Be, Si, Sn, Al and Ga), and Ni—Al alloys containing 36 to 38 at % of Al. Among these, the Ni—Ti alloys are particularly preferred. The superelastic alloys represented by the Ni—Ti alloys are excellent also in adhesion of a resin coating layer 8 which will be described later.

Cobalt alloys each show a high modulus of elasticity when formed into wires, and each have an appropriate elastic modulus. Therefore, a wire comprised of a cobalt alloy is excellent in torque transmission performance, and is not likely to be susceptible to problems such as buckling. The cobalt alloy to be used here may be any alloy that contains Co as a constituent element. However, alloys containing Co as a main constituent (Co-based alloys, namely, alloys in which the content of Co by weight is the highest of the contents of constituent elements) are preferred, and Co—Ni—Cr alloys are more preferred. When an alloy with such a composition is used, the above-mentioned effect becomes more conspicuous. In addition, an alloy with such a composition has a high modulus of elasticity, and can be cold deformed notwithstanding the elastic limit set to be high. The high elastic limit makes it possible to reduce the wire diameter while sufficiently preventing generation of buckling, and therefore to obtain a guide wire having rigidity and flexibility sufficient for insertion to a desired site.

As the material constituting the second wire 4, the above-mentioned stainless steels are preferable. Stainless steels are higher in strength and rigidity than the above-mentioned superelastic alloys, and can therefore provide the guide wire 1 with excellent pushability and torque transmission performance.

The first wire 2 and the second wire 4 may be comprised of different materials, or may be comprised of the same metallic material or of metallic materials of the same type (alloys which contain the same main metallic elements). In the latter case, the joint part (weld part) 6 has a higher joint strength, so that even when the outer diameter of the joint part 6 is relatively small, disconnection or the like is inhibited or prevented and a good torque transmission performance and the like are displayed.

In the case where the first wire 2 and the second wire 4 are comprised of different materials, the first wire 2 is preferably comprised of the above-mentioned superelastic alloy, more preferably a Ni—Ti alloy, while the second wire 4 is preferably comprised of the above-mentioned stainless steel.

The embodiment of the guide wire described above involves a first wire 2 and a second wire 4 joined to each other. However, it is also possible for the guide wire to be composed of a single continuous wire body integrally formed in one piece so as to be free of a joint part. In that case, examples of the material constituting the wire body include the same materials as mentioned above, among which particularly preferred are the stainless steels, the cobalt alloys, and the pseudo-elastic alloys.

The coil 5 is disposed around the outer periphery of the distal part of the wire body 10 to cover the distal part. With the coil 5 thus arranged, the area of contact of the wire body 10 with the inside wall of a catheter or the surface of a living body is reduced, whereby frictional resistance is lowered. As a result, the guide wire 1 possesses further enhanced operationality. The coil 5 preferably has a longitudinal extent by which the coil 5 at least covers (i.e., is longitudinally coextensive with) the reshapeable section 3 from the distal most bent part 31 to the proximal most bent part 35.

As shown in FIG. 1, the wire body 10 is located in a central part of the inside of the coil 5. In the present embodiment, the coil 5 covers (i.e., is longitudinally co-extensive with the reshapeable section 3, the transition section 27, the distal-side constant outer diameter section 26, the first tapered section 22, and the entire constant outer diameter section 21 or a part of the constant outer diameter section 21.

In addition, the distal part of the wire body 10 (particularly, the region ranging from the reshapeable section 3 to the first tapered section 22) is located relative to the coil 5 such that the outer surface of the distal part of the wire body 10 is spaced from and out of contact with the inside surface of the coil 5. This results in gap 50 between the coil 5 and the distal part of the wire body 10.

The coil 5 is obtained by helically forming a filament 54 which is circular in cross-sectional shape. In this case, the coil 5 may be composed of a single filament 54 wound helically or of a plurality of filaments 54 wound helically.

The material constituting the filament 54 is not particularly limited. Examples of suitable material include a metallic material or a resin material. Examples of the metallic material include stainless steel, and radiopaque materials such as Pt—Ni alloys. In the latter case, radiopacity can be obtained at the distal part of the guide wire 1, and the guide wire 1 can be inserted into a living body while checking the position of the distal part under fluoroscopic observation, which naturally is preferable.

The coil 5 may be formed by combining two or more materials. For example, a configuration may be adopted in which the coil is formed of two filaments, one filament on the distal side of the coil 5 comprised of a radiopaque material such as a Pt—Ni alloy, and another filament on the proximal side of the coil 5 comprised of stainless steel. In this case, under fluoroscopic observation, the portion located on the distal side of the coil 5 can be exaggerated (can be visually checked more easily) as compared with the portion located on the proximal side. Thus, the position of the distal most portion of the guide wire 1 (the portion where the reshapeable section 3 is present) can be visually observed more clearly.

In addition, the wire diameter of the filament 54 of the coil 5 may be constant over the whole length of the coil 5, or may differ on the distal side and on the proximal side of the coil 5. For example, the wire diameter of the filament 54 on the distal side of the coil 5 may be smaller than that on the proximal side. This further enhances the flexibility of the guide wire 1 at the distal part of the coil 5. The wire diameter of the filament 54 on the distal side of the coil 5 may be larger than that on the proximal side. This makes further enhances the radiopacity of the guide wire 1 at a distal part of the coil 5.

The outer diameter of the overall coil 5 may be constant over the whole length of the coil 5, or may differ on the distal side and on the proximal side of the coil 5. For example, the outer diameter of the overall coil 5 on the distal side of the coil 5 may be smaller than that on the proximal side. This further enhances the flexibility of the guide wire 1 at a distal part of the coil 5.

The adjacent turns of the filament 54 of the coil 5 may be in contact with each other in the absence of an externally applied force, i.e., the coil 5 is characterized by a so-called close (tight) winding. Alternatively, the adjacent turns of the filament 54 of the coil 5 may be spaced from each other in at least some part(s) of the coil 5 in the absence of an externally applied force. At least the portion of the coil 5 disposed around the reshapeable section 3 preferably has adjacent windings that are spaced from one another. The spaced adjacent windings of coil 5 and the zig-zag shaped reshapeable section 3 help impart shock absorber characteristics to the most-distal end of the guide wire 1 in the event it bumps against a wall of an artery.

The coil 5 is fixed to the wire body 10 at a plurality of locations. As illustrated in FIG. 1, the coil 5 is fixed to the wire body 10 at three locations. Specifically, a distal part of the coil 5 is fixed to the distal end of the first wire 2 (the distal end of the reshapeable section 3) by a fixing material or fixing part 51, a proximal part of the coil 5 is fixed to an intermediate part of the first wire 2 (in the vicinity of the boundary between the constant outer diameter section 21 and the second tapered section 23) by a fixing material or fixing part 53, and an intermediate part of the coil 5 is fixed to the first tapered section 22 of the first wire 2 by a fixing material or fixing part 52. With the coil 5 fixed at a plurality of locations such as those illustrated, parts of the coil 5 can be securely fixed to the wire body 10 without significantly negatively influencing the flexibility of the distal part of the guide wire 1 (the part where the coil 5 is present).

Particularly, since the reshapeable section 3 is fixed on the distal side (distal part) and the proximal side (proximal part) by the fixing materials 51, 52, the reshapeable section 3 can be assuredly fixed to the coil 5 so that the shape of the reshapeable section 3 upon reshaping can be appropriately maintained.

The fixing materials 51, 52, 53 are each preferably comprised of a solder (brazing filler metal). Each of the fixing materials 51, 52, 53 is not limited to solder, but may be an adhesive. In addition, the method of fixing the coil 5 to the wire body 10 is not limited to the use of the fixing material(s) but may involve welding, for example. A distal end surface of the fixing material 51 is preferably rounded as shown in FIG. 1 in order to prevent it from damaging the inside wall of a body lumen such as a blood vessel.

While the fixing material 52 is disposed on the first tapered section 22 in the illustrated configuration, the location of the fixing material 52 is not limited in this regard. The fixing material 52 may be disposed at any intermediate portion of the coil 5, provided the portion is located on the proximal side of the reshapeable section 3.

As shown in FIG. 1, the outside surface of the guide wire 1 is provided with a resin coating layer 8 covering the entire outside surface, or a part of the outside surface. The resin coating layer 8 may be formed for any of a variety of purposes. One example is to reduce the friction (sliding resistance) of the guide wire 1 and enhance slidability, thereby enhancing the operational aspects of the guide wire 1.

In order to reduce the friction (sliding resistance) of the guide wire 1, the resin coating layer 8 is preferably comprised of a material capable of reducing friction as described below. This helps ensure that the frictional resistance (sliding resistance) between the guide wire 1 and the inside wall of a catheter used therewith is reduced, and the slidability of the guide wire 1 is enhanced, whereby the operational characteristics of the guide wire 1 in the catheter are further enhanced. In addition, the reduction of the sliding resistance of the guide wire 1 helps ensure that, when the guide wire 1 is moved and/or rotated in a catheter, it is possible to more securely prevent the guide wire 1 from kinking (sharply bending) or torsion, particularly to more assuredly prevent a guide wire portion near the joint part 6 from kinking or becoming plastically damaged by torsional force.

Examples of materials capable of reducing friction include polyolefins such as polyethylene, polypropylene, etc., polyvinyl chloride, polyesters (PET, PBT, etc.), polyamides, polyimides, polyurethane, polystyrene, polycarbonate, silicone resins, fluororesins (PTFE, ETFE, etc.), and composite materials of these.

The resin coating layer 8 may be formed also for the purpose of enhancing safety in inserting the guide wire 1 into a blood vessel or the like. For this purpose, the resin coating material 8 is preferably comprised of a material rich in flexibility (soft material, elastic material).

Examples of materials rich in flexibility include polyolefins such as polyethylene, polypropylene, etc., polyvinyl chloride, polyesters (PET, PBT, etc.), polyamides, polyimides, polyurethane, polystyrene, silicone resins, thermoplastic elastomers such as polyurethane elastomers, polyester elastomers, polyamide elastomers, etc., various rubber materials such as latex rubbers, silicone rubbers, etc., and composite materials obtained by combining two or more of these.

The resin coating layer 8 need not necessarily be comprised entirely of the same material. That is, different materials may be used on the distal side and on the proximal side of an intermediate part of the guide wire 1. For example, a configuration may be adopted in which the portion of the resin coating layer 8 covering the first wire 2 and the coil 5 is comprised of the above-mentioned material rich in flexibility, whereas the portion of the resin coating layer 8 covering the second wire 4 is comprised of the above-mentioned material capable of reducing friction.

In addition, the resin coating layer 8 may be a single layer or a laminate of two or more layers (for example, a laminate in which an inner layer is comprised of a material softer than the material constituting an outer layer). For example, a configuration may be adopted in which the portion of the resin coating layer 8 covering the first wire 2 and the coil 5 is a single layer, whereas the portion of the resin coating layer 8 covering the second wire 4 is a laminate of two or more layers, or vice versa.

The outside surface of at least a distal part of the guide wire 1 is preferably coated with a hydrophilic material. This helps ensure that the hydrophilic material when wetted exhibits lubricity, whereby the friction (sliding resistance) of the guide wire 1 is reduced and the slidability of the guide wire 1 is enhanced. As a result, the operationality of the guide wire 1 is enhanced.

Examples of the hydrophilic material include cellulose polymeric materials, polyethylene oxide polymeric materials, maleic anhydride polymeric materials (for example, a maleic anhydride copolymer such as methyl vinyl ether-maleic anhydride copolymer), acrylamide polymeric materials (for example, polyacrylamide, polyglycidyl methacrylate-dimethyl acrylamide (PGMA-DMAA) block copolymer), water-soluble nylon, polyvinyl alcohol, and polyvinyl pyrrolidone.

Such hydrophilic materials, in many cases, exhibit lubricity through wetting (absorption of water), thereby reducing the frictional resistance (sliding resistance) between the guide wire 1 and the inside wall of a catheter with which the guide wire is used. As a result, the slidability of the guide wire 1 is enhanced, and the operationality of the guide wire 1 in the catheter will be better.

Figure 4:
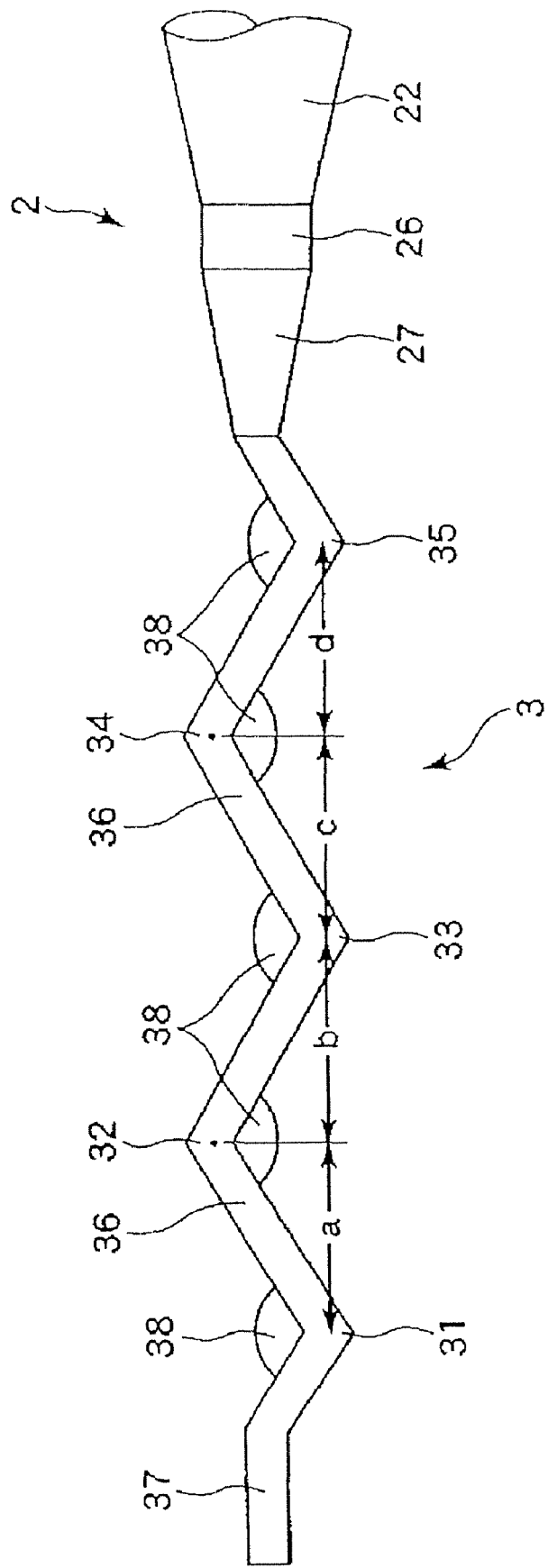
FIG. 4 is a side view of a reshapeable section according to a second embodiment of the guide wire disclosed.

FIG. 4 is a side view showing the configuration of a reshapeable section of a guide wire according to another embodiment.

The following description will primarily describe aspects of the second embodiment of the guide wire which differ from the first embodiment described above. Features in the second embodiment of the guide wire that are the same as or similar to those in the first embodiment are identified by the same reference numerals used in the first embodiment, and a detailed description of such features will not be repeated.

This second embodiment is the same as the first embodiment described above, except that the configuration of the reshapeable section 3 is different.

As shown in FIG. 4, the reshapeable section 3 is plate-like in shape, and possesses, along its longitudinal extent, a plurality of bent parts that are bent in opposite directions in the same manner as in the first embodiment above. In the illustrated embodiment, the plurality of bent parts includes a total of five bent parts 31, 32, 33, 34, 35.

Each of the bent parts 31-35 is accompanied by a malleable metal 38 secured to the recessed part side (the inner side) thereof by such a method as flame spraying, welding, plating, vapor deposition, sputtering, etc. Thus, the malleable metal 38 is located on the interior angle formed by each bent part 31-35. When a bending stress is exerted on one of the bent parts 31-35, the malleable metal 38 secured to such bent part undergoes plastic deformation (spreading, compression or the like), resulting in plastic deformation of the bent part as a whole, and the shape upon this deformation is generally maintained.

Such a configuration helps impart to the bent parts 31-35 the property of being more susceptible to plastic deformation, that is the property of more likely maintaining s deformed shape upon deformation, as compared with parts of the reshapeable section 3 other than the bent parts (for example, the straight parts 36 between the adjacent bent parts, or a part 37 on the distal side of the bent part 31). Therefore, when the reshapeable section 3 is reshaped, the bent parts 31-35 are deformed (plastically deformed) more readily than, or with priority over, the other parts so that they can be reshaped into a desired shape relatively easily and assuredly, and the resulting shape is maintained. The reshapeable section 3 thus reshaped maintains the reshaped shape not only at normal temperature but also when its temperature is raised roughly to a body temperature.

This embodiment does not utilize a configuration in which the malleable metal is secured to the entire longitudinal extent of the reshapeable section 3 to render the entire reshapeable section 3 susceptible to plastic deformation. Instead, in this embodiment, the malleable metal is secured to spaced apart portions of the reshapeable section 3 so that only parts of the reshapeable section 3 are rendered susceptible to plastic deformation. More specifically, the malleable metal is secured to the spaced bent parts 31-35 of the reshapeable section 3 so that only the bent parts 31-35 are rendered susceptible to plastic deformation. This makes it possible to address and preferably overcome drawbacks associated with other known guide wires such as the problem that the reshapeable section 3 as a whole is hardened more than necessary, thereby lowering the flexibility or elasticity of the distal part of the guide wire 1.

The malleable material 38 is preferably different in composition from the material comprising the reshapeable section 3. Examples of the malleable metal 38 include Au and Au alloys (for example, Au—Cu alloys containing 1 to 50 wt % of Cu, Au—Ag alloys containing 1 to 50 wt % of Ag, and Au—Pt alloys containing 1 to 50 wt % of Pt). Here, Au and Au alloys (particularly, Au—X alloys containing 1 to 50 wt % of X, where X is at least one selected from among Cu, Ag and Pt) are excellent in malleability and in adhesion to the bent parts 31-35, and also in chemical stability, and are therefore preferable.

The amount (weight) of the malleable metal 38 secured respectively to the bent parts 31-35 may be the same or different. For example, the amount (weight) of the malleable metal 38 secured to the interior angle of the bent parts may be gradually increased or decreased along the distal direction of the reshapeable section 3 (namely, sequentially in the order of the bent parts 35, 34, 33, 32 and 31). In the former case (the amount is increased), the susceptibility of the reshapeable section 3 to plastic deformation increases as the distal end of the reshapeable section 3 is approached. In the latter case (the amount is decreased), the susceptibility of the reshapeable section 3 to plastic deformation increases as the proximal end of the reshapeable section 3 is approached.

In addition, the composition of the malleable metals 38 secured respectively to the bent parts 31-35 may be the same or different. For example, a configuration may be adopted in which Au (pure gold) is used as the malleable metal 38 for the bent parts 31 and 32 relatively located on the distal side of the reshapeable section 3, whereas an Au—X alloy or alloys containing 1 to 50 wt % of X (for example, an Au—Cu alloy containing 1 to 50 wt % of Cu) is used as the malleable metal(s) 38 for the other bent parts 33-35.

Also, in this illustrated embodiment, the malleable material 38 is secured to every one of the bent parts 31-35. However, variations on this arrangement are possible depending upon the desired objectives. For example, the malleable metal 38 may be secured to less than all of the bent parts so long as the malleable material is secured to at least one of the bent parts 31-35.

Figure 5:
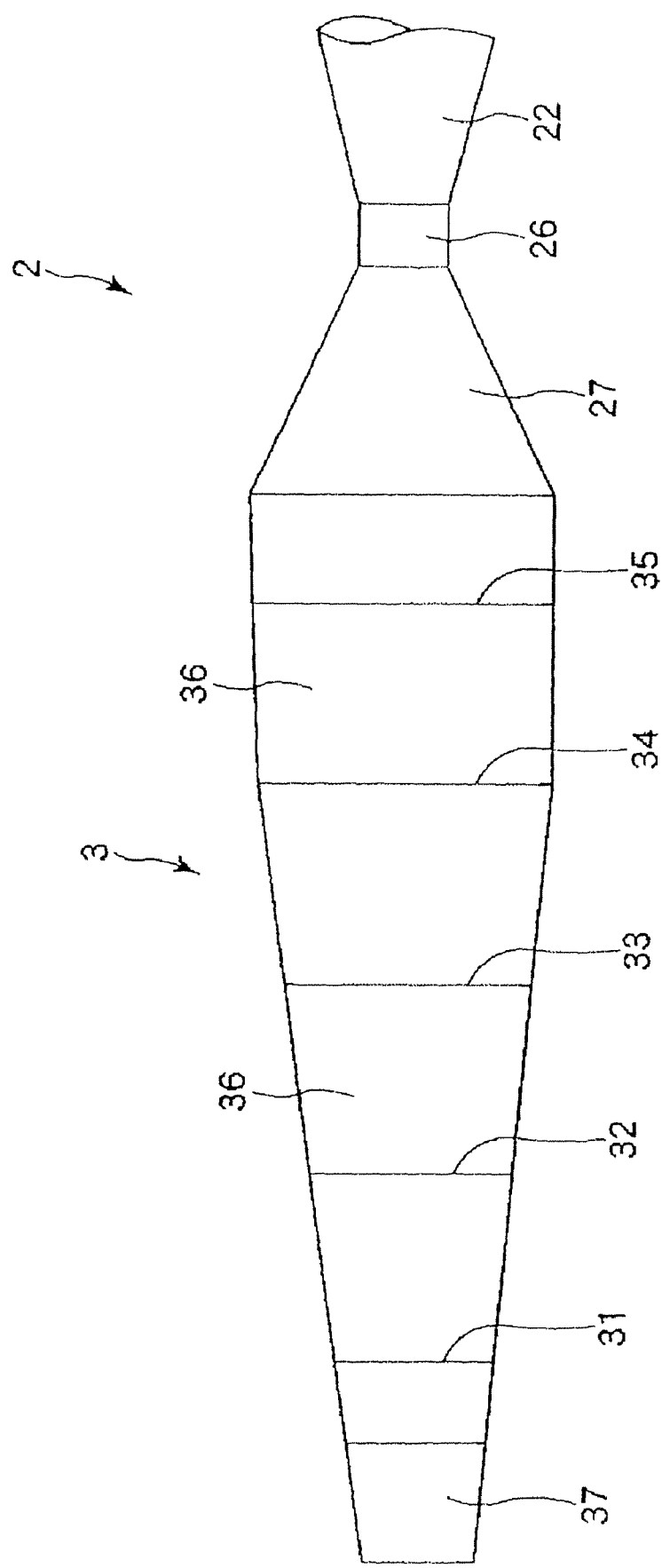
FIG. 5 is a plan view of a reshapeable section according to a third embodiment of the guide wire disclosed here.

FIG. 5 is a plan view of a third embodiment of a guide wire with a reshapeable section.

The following description will primarily describe aspects of the third embodiment of the guide wire which differ from the first embodiment described above. Features in the third embodiment of the guide wire that are the same as or similar to those in the first embodiment are identified by the same reference numerals used in the first embodiment, and a detailed description of such features is not repeated.

This embodiment of the guide wire is the same as the first embodiment described above, except for differences in the configuration of the reshapeable section 3.

As shown in FIG. 5, the reshapeable section 3 is plate-like in shape, and possesses, along its longitudinal extent, a plurality of bent parts that are bent in opposite directions in the same manner as in the first embodiment above. In this illustrated embodiment, like the earlier embodiments, the plurality of bent parts includes a total of five bent parts 31, 32, 33, 34, 35.

In the first embodiment above, the plate width of the reshapeable section 3 is constant along the entire longitudinal extent of the reshapeable section 3. This third embodiment differs in that the reshapeable section 3 has a part where the plate width gradually decreases in the distal direction. Specifically, in the part on the distal side of the bent part 34 of the reshapeable section 3, the width of the reshapeable section 3 gradually decreases in the distal direction.

This configuration contributes to the reshapeable section 3 being reshaped more finely as the distal end thereof is approached. In other words, the reshapeable section 3 can be reshaped into a more complicated or finer shape (for example, a more acutely curved or bent shape) on the distal side than on the proximal side.

It is also possible to adopt a configuration in which the width of the reshapeable section 3 decreases stepwise in the distal direction in at least some part of the reshapeable section 3.

Figure 6:
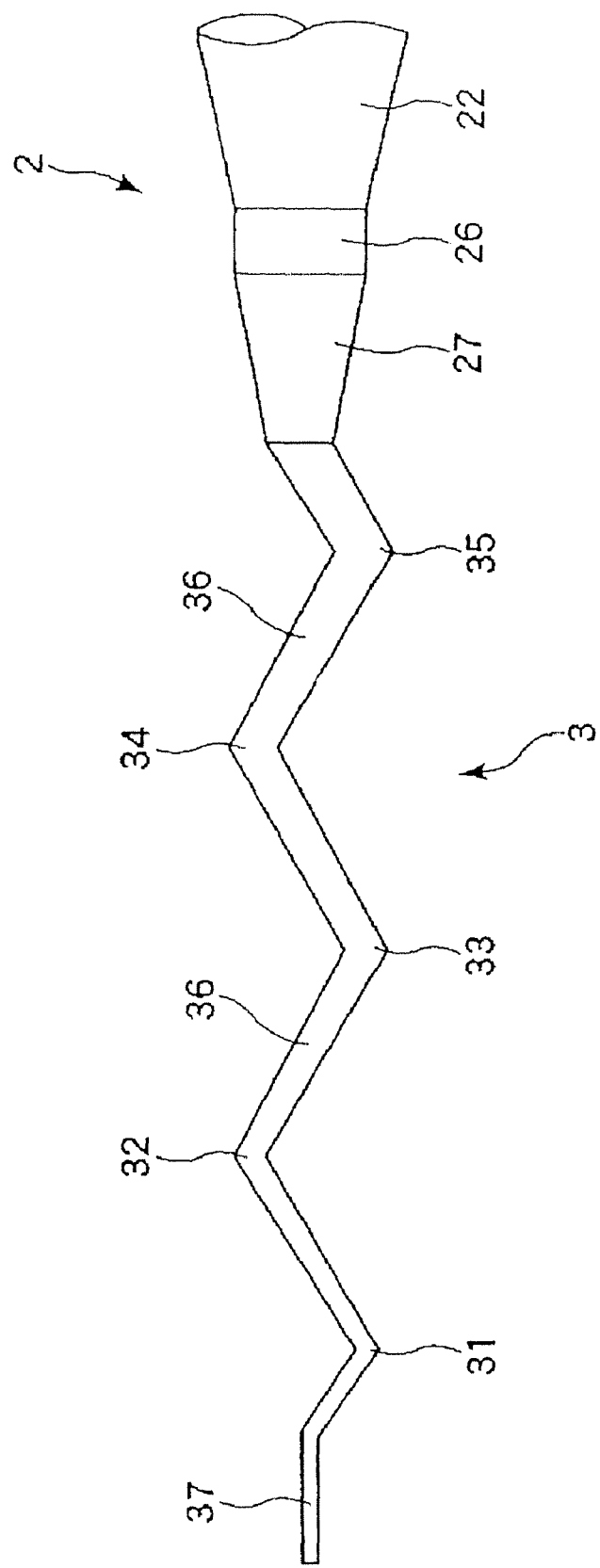
FIG. 6 is a side view of a reshapeable section according to a fourth embodiment of the guide wire disclosed here.

FIG. 6 is a side view of a fourth embodiment of a guide wire with a reshapeable section.

The following description will primarily describe aspects of the fourth embodiment of the guide wire which differ from the first embodiment described above. Features in the fourth embodiment of the guide wire that are the same as or similar to those in the first embodiment are identified by the same reference numerals used in the first embodiment, and a detailed description of such features is not repeated.

This fourth embodiment of the guide wire is the same as the first embodiment, except that the configuration of the reshapeable section 3 differs.

As shown in FIG. 6, the reshapeable section 3 is plate-like in shape, and possesses, along its longitudinal extent, a plurality of bent parts that are bent in opposite directions in the same manner as in the first embodiment above. In this illustrated embodiment, like the earlier embodiments, the plurality of bent parts includes a total of five bent parts 31, 32, 33, 34, 35.

In the first embodiment described above, the thickness of the reshapeable section 3 is constant along the entire longitudinal extent of the reshapeable section 3. The fourth embodiment of the guide wire differs in this regard in that the reshapeable section 3 has a part where the thickness gradually decreases (continuously decreases) in the distal direction. Specifically, in the part on the distal side of the bent part 35 (or the bent part 34) of the reshapeable section 3, the thickness of the reshapeable section 3 gradually decreases along the distal direction.

This configuration permits the reshapeable section 3 to be reshaped more finely as the distal end of the reshapeable section 3 is approached. More specifically, the reshapeable section 3 can be reshaped into a more complicated or finer shape (for example, a more acutely curved or bent shape) on the distal side than on the proximal side.

It is also possible to adopt a different configuration in which the reshapeable section 3 has a part where the thickness of the plate-shaped reshapeable section 3 decreases stepwise along the distal direction.

Also, it is possible to configure a guide wire to include the reshapeable section 3 embodying both the varying width of the third embodiment and the varying thickness of the fourth embodiment. To be more specific, a configuration may be adopted in which the plate-shaped reshapeable section 3 has a part where both the width and the thickness decreases, continuously or stepwise, along the distal direction. In this case, the effect by which the reshapeable section 3 can be reshaped into a more complicated or finer shape on the distal side than on the proximal side is displayed more remarkably.

It is to be understood that it is possible to configure a guide wire in which two or more of the embodiments disclosed here are combined. Also, the number and shapes of the bent parts in the reshapeable section 3 are not limited to those illustrated in the drawing figures.

The principles, embodiments and modes of operation have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. For example, parts or features of the guide wire can be replaced by other features or parts exhibiting the same or similar functional characteristics. In addition, features beyond those described here can be used in the guide wire. Accordingly, it is expressly intended that all such variations, changes and equivalents which fall within the spirit and scope of the present invention as defined in the claims, be embraced thereby.

What is claimed is:

1. A guide wire comprising:
a wire body possessing a distal portion and a proximal portion, the proximal portion being positioned proximally of the distal portion and being coaxial with the distal portion;
the distal portion of the wire body comprising a reshapeable section, possessing a width and a thickness, the thickness of the reshapeable section being less than the width of the reshapeable section;
the reshapeable section comprising a plurality of spaced apart bent parts and a plurality of spaced apart interposed parts, with adjacent ones of the bent parts being spaced apart by one of the interposed parts, the adjacent ones of the interposed parts being non-coplanar with one another so that the reshapeable section possesses an overall zig-zag shape;
at least one of the bent parts possessing plastic deformation characteristics different from one of the interposed parts of the zig-zag shaped reshapeable section so that the at least one bent part is more easily plastically deformed than the one interposed part of the zig-zag shaped reshapeable section; and
wherein the at least one bent part that is more easily plastically deformed includes a malleable metal secured to the at least one bent part at spaced apart locations.

2. The guide wire as set forth in claim 1, wherein the at least one bent part that is more easily plastically deformed is a work-hardened bent part.

3. The guide wire as set forth in claim 1, wherein the at least one bent part that is more easily plastically deformed is an annealed bent part.

4. The guide wire as set forth in claim 1, wherein the at least one bent part that is more easily plastically deformed possesses an interior angle and an exterior angle greater than the interior angle, the malleable metal being positioned in the interior angle of the at least one bent part.

5. The guide wire as set forth in claim 1, wherein the reshapeable section possesses a thickness and a width, the thickness and/or the width of at least a portion of the reshapeable section decreasing in the distal direction.

6. The guide wire as set forth in claim 5, wherein the thickness and/or the width of at least a portion of the reshapeable section decreases continuously in the distal direction.

7. The guide wire as set forth in claim 1, further comprising a coil encircling the reshapeable section, the coil possessing an interior surface and the reshapeable section possessing an exterior surface, the plurality of bend parts comprising a distal most bent part and a proximal most bent part, the coil having a longitudinal extent by which the coil covers the reshapeable section at least from the distal most bent part to the proximal most bent part.

8. The guide wire as set forth in claim 1, wherein the plurality of bent parts comprises at least first, second and third bent parts, with the second bent part positioned between the first and third bent parts, and the third bent part located closer to the proximal portion of the wire body, and wherein a distance between the first and second bent parts as measured parallel to a longitudinal extent of the guide wire is equal to the distance between the second and third bent parts as measured parallel to the longitudinal extent of the guide wire.

9. A guide wire comprising:
   a wire body comprised of a plate-shaped reshapeable section, the plate-shaped reshapeable section being located at a distal part of the wire body;
   the plate-shaped reshapeable section comprising a plurality of bent parts disposed along a longitudinal extent of the plate-shaped reshapeable section, adjacent ones of the bent parts being bent in opposite directions;
   at least one of the bent parts being more susceptible to plastic deformation than another part of the plate-shaped reshapeable section; and
   wherein the at least one bent part that is more susceptible to plastic deformation includes a malleable metal secured to the at least one bent part at spaced apart locations.

10. The guide wire as set forth in claim 9, wherein the at least one bent part that is more susceptible to plastic deformation is a work-hardened bent part.

11. The guide wire as set forth in claim 9, wherein the at least one bent part that is more susceptible to plastic deformation is an annealed bent part.

12. The guide wire as set forth in claim 9, wherein the reshapeable section possesses a thickness and a width, the thickness and/or the width of at least a portion of the reshapeable section decreasing in the distal direction.

13. The guide wire as set forth in claim 12, wherein the thickness and/or the width of at least a portion of the reshapeable section decreases continuously in the distal direction.

14. The guide wire as set forth in claim 9, wherein the plurality of bent parts comprises at least first, second and third bent parts, with the second bent part positioned between the first and third bent parts, and the third bent part located closer to the proximal portion of the wire body, and wherein a distance between the first and second bent parts as measured parallel to a longitudinal extent of the guide wire is equal to the distance between the second and third bent parts as measured parallel to the longitudinal extent of the guide wire.

* * * * *